United States Patent
Ichihashi

(10) Patent No.: US 12,172,032 B2
(45) Date of Patent: Dec. 24, 2024

(54) IRRADIATION CONTROL APPARATUS, RADIOTHERAPY SYSTEM, AND IRRADIATION CONTROL METHOD

(71) Applicant: Canon Medical Systems Corporation, Otawara (JP)

(72) Inventor: Masahide Ichihashi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 951 days.

(21) Appl. No.: 17/206,798

(22) Filed: Mar. 19, 2021

(65) Prior Publication Data

US 2021/0290977 A1 Sep. 23, 2021

(30) Foreign Application Priority Data

Mar. 23, 2020 (JP) ................. 2020-051625

(51) Int. Cl.
| | |
|---|---|
| *A61N 5/10* | (2006.01) |
| *G06N 20/00* | (2019.01) |
| *G16H 30/40* | (2018.01) |
| *G16H 50/20* | (2018.01) |

(52) U.S. Cl.
CPC .......... *A61N 5/1049* (2013.01); *G06N 20/00* (2019.01); *G16H 30/40* (2018.01); *G16H 50/20* (2018.01); *A61N 2005/1055* (2013.01); *A61N 5/1081* (2013.01)

(58) Field of Classification Search
CPC .......... A61N 5/1049; A61N 2005/1055; A61N 5/1067; G16H 20/40; G16H 50/20; G16H 30/40
See application file for complete search history.

(56) References Cited

U.S. PATENT DOCUMENTS

| | | | |
|---|---|---|---|
| 10,255,723 B2 | 4/2019 | Thomas et al. | |
| 2011/0266464 A1* | 11/2011 | Takai | A61N 5/107 703/2 |
| 2014/0046172 A1* | 2/2014 | Kim | A61B 8/085 600/407 |
| 2020/0242762 A1 | 7/2020 | Matsuki et al. | |

FOREIGN PATENT DOCUMENTS

| | | |
|---|---|---|
| JP | 2016-517288 A | 6/2016 |
| JP | 2016-158890 A | 9/2016 |
| JP | 2019-074868 A | 5/2019 |
| WO | WO 2019/146358 A1 | 8/2019 |

OTHER PUBLICATIONS

Japanese Office Action issued Jan. 4, 2024 in Japanese Application 2020-051625, (with unedited computer-generated English translation), 4 pages.

* cited by examiner

*Primary Examiner* — Gerald Johnson
(74) *Attorney, Agent, or Firm* — Oblon, McClelland, Maier & Neustadt, L.L.P.

(57) ABSTRACT

According to one embodiment, an irradiation control apparatus includes processing circuitry. The processing circuitry obtains an MR image of a first time phase, which includes a tumor region of a patient. The processing circuitry estimates a position of the tumor region of the patient of a second time phase from the MR image of the first time phase, the second time phase being a predetermined time phase after the first time phase. The processing circuitry controls irradiation by a radiotherapy apparatus based on the estimated tumor position of the second time phase.

17 Claims, 11 Drawing Sheets

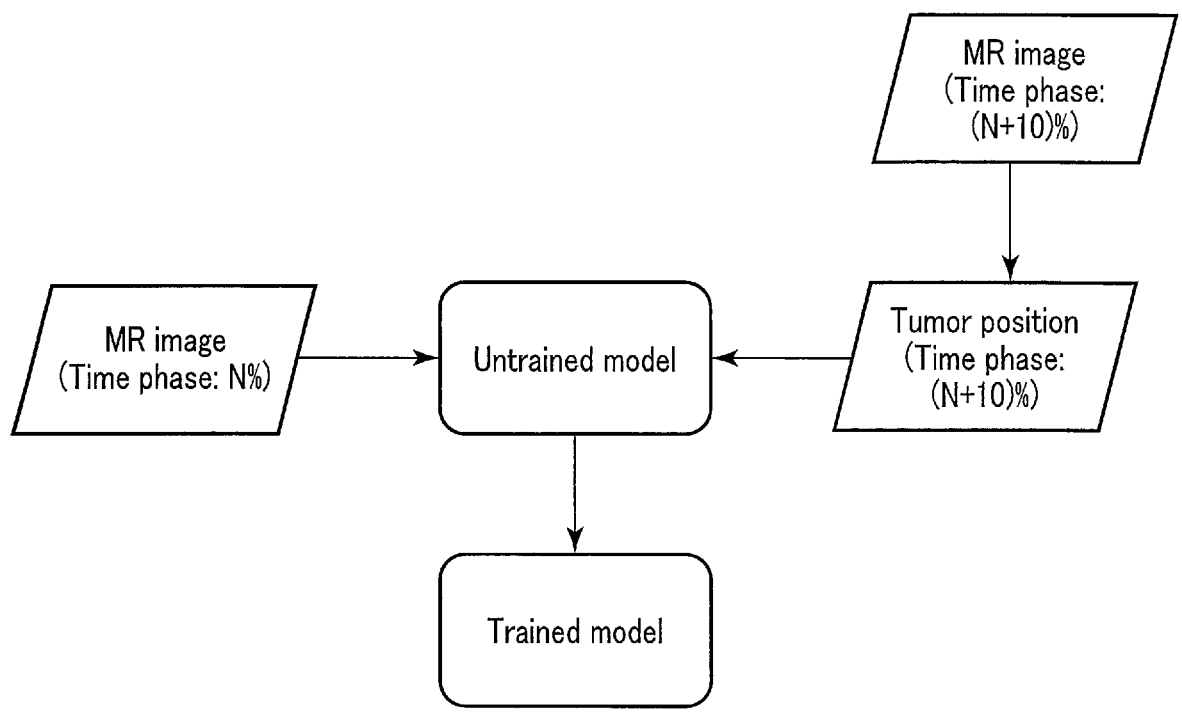
F I G. 6

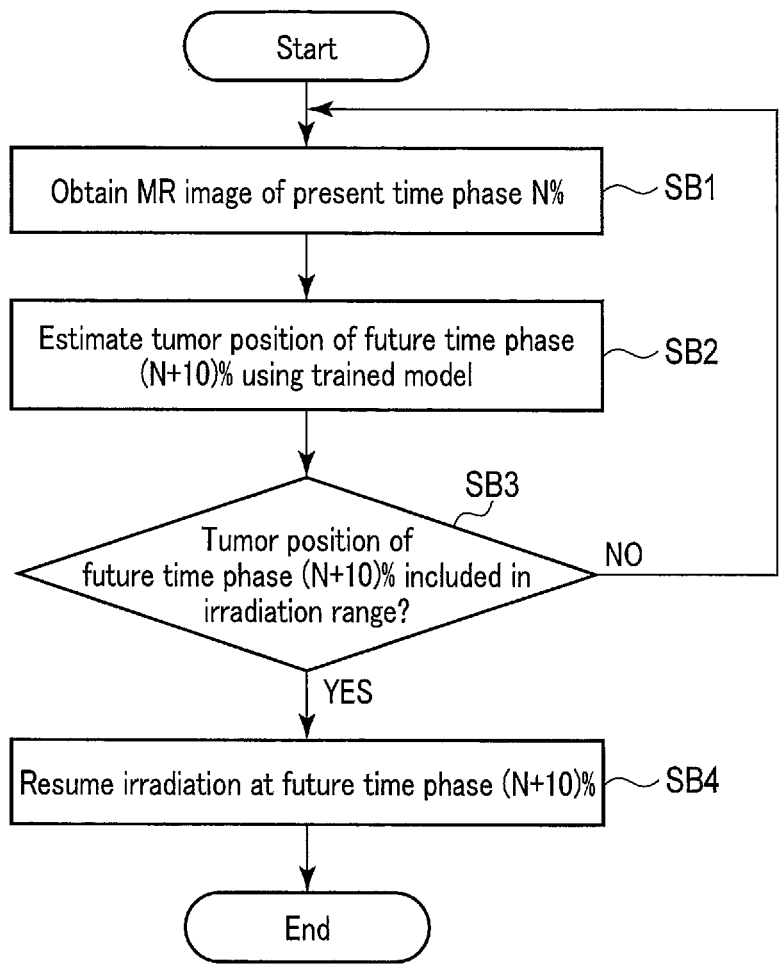
F I G. 11

IRRADIATION CONTROL APPARATUS, RADIOTHERAPY SYSTEM, AND IRRADIATION CONTROL METHOD

CROSS-REFERENCE TO RELATED APPLICATIONS

This application is based upon and claims the benefit of priority from the Japanese Patent Application No. 2020-051625, filed Mar. 23, 2020 the entire contents of which are incorporated herein by reference.

FIELD

Embodiments described herein relate generally to an irradiation control apparatus, a radiotherapy system, and an irradiation control method.

BACKGROUND

There is an magnetic resonance imaging (MRI) integrated radiotherapy system, in which a magnetic resonance imaging apparatus is integrated with a radiotherapy apparatus. The MRI integrated radiotherapy system can perform MR imaging on a patient, identify a position of a tumor by image processing, and control irradiation in accordance with the position of the tumor, during irradiation. However, the image processing requires time; therefore, the actual tumor position may have moved out of the irradiation range when irradiation control is performed.

BRIEF DESCRIPTION OF THE DRAWINGS

FIG. 6 is a schematic diagram of processing for generating a trained model by a machine learning apparatus in FIG. 1.

FIG. 11 is a diagram showing another example of the flow of irradiation control by the irradiation control apparatus.

DETAILED DESCRIPTION

An irradiation control apparatus according to an embodiment includes processing circuitry. The processing circuitry obtains an MR image of a first time phase, which includes a tumor region of a patient. The processing circuitry estimates a position of the tumor region of the patient of a second time phase from the MR image of the first time phase, the second time phase being a predetermined time phase after the first time phase. The processing circuitry controls irradiation by a radiotherapy apparatus based on the estimated tumor position of the second time phase.

Hereinafter, an embodiment of the irradiation control apparatus, radiotherapy system, and irradiation control method will be described in detail with reference to the accompanying drawings.

Figure 1:
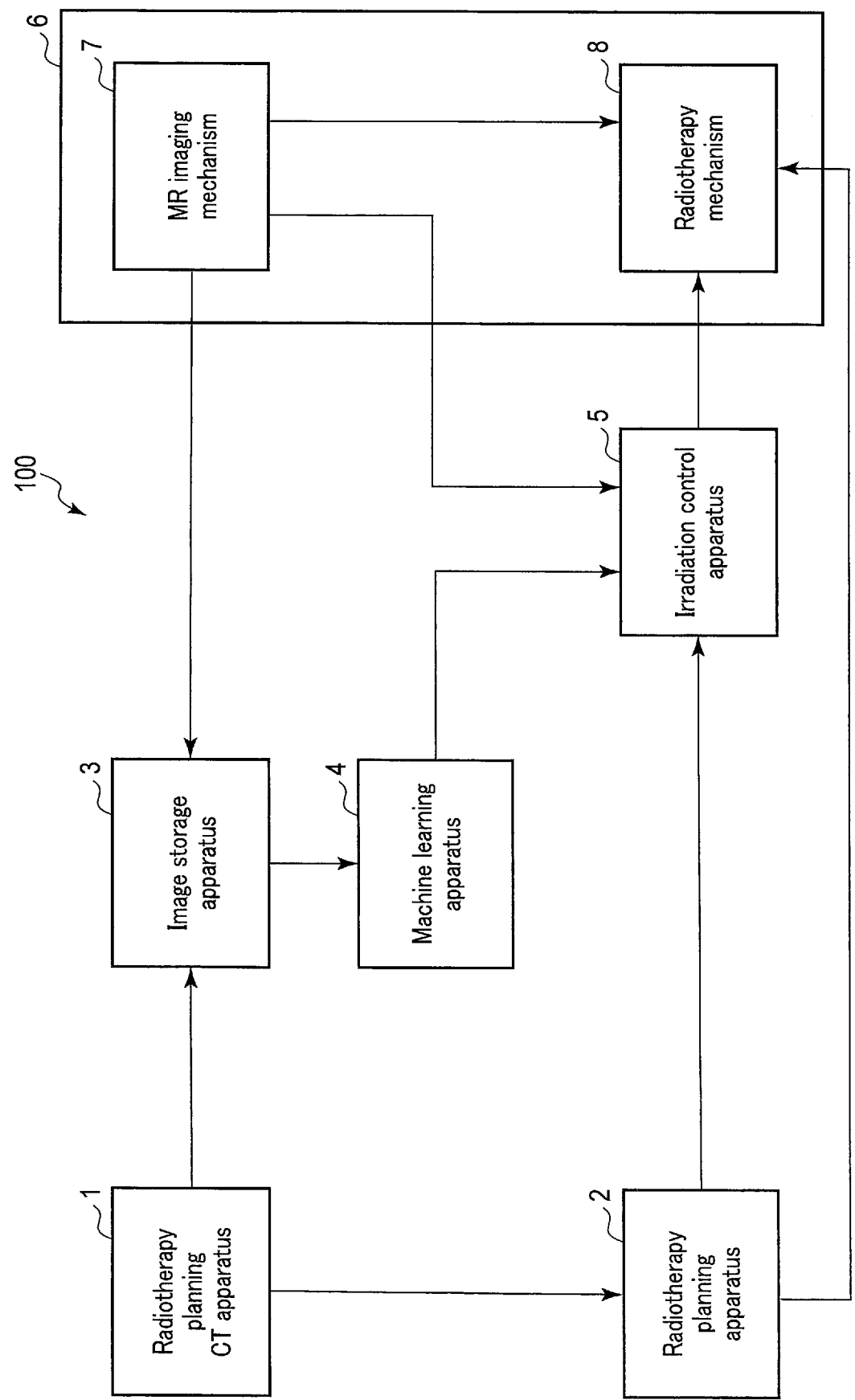
FIG. 1 is a diagram showing a configuration example of a radiotherapy system according to the present embodiment.

FIG. 1 is a diagram showing a configuration example of a radiotherapy system 100 according to the present embodiment. As shown in FIG. 1, the radiotherapy system 100 includes a radiotherapy planning computed tomography (CT) apparatus 1, a radiotherapy planning apparatus 2, an image storage apparatus 3, a machine learning apparatus 4, an irradiation control apparatus 5, and an MRI integrated radiotherapy apparatus 6.

The radiotherapy planning CT apparatus 1 is an X-ray computed tomography apparatus for generating a CT image used for radiotherapy planning. The radiotherapy planning CT apparatus 1, for example, irradiates a patient with X-rays through an X-ray tube while rotating, at high speed, a rotatable frame which holds the X-ray tube and an X-ray detector, and detects X rays that have passed through the patient using the X ray detector. The radiotherapy planning CT apparatus 1 then generates a CT image that expresses spatial distribution of the X-ray attenuation coefficients of substances on the X-ray transmission path, based on raw data from the X-ray detector. The CT image generated by the radiotherapy planning CT apparatus 1 is called a "radiotherapy planning CT image". The radiotherapy planning CT image is supplied to the radiotherapy planning apparatus 2 and the image storage apparatus 3.

The radiotherapy planning apparatus 2 is a computer including a processor such as a central processing unit (CPU), a memory such as a read only memory (ROM) or a random access memory (RAM), a display, an input interface, and a communication interface. The radiotherapy planning apparatus 2 is a computer that forms a radiotherapy plan for the patient using the radiotherapy planning CT image. There are two types of methods for forming a radiotherapy plan, namely, forward planning and inverse planning. The radiotherapy planning apparatus 2 determines dose distribution as a radiotherapy plan, based on radiotherapy conditions, such as the number of irradiation gates, the irradiation angle, the radiation intensity, and the degree of opening of the collimator for radiotherapy. The radiotherapy plan is supplied to the irradiation control apparatus 5 and the MRI integrated radiotherapy apparatus 6.

The image storage apparatus 3 is a computer including a mass storage, such as a hard disk drive (HDD), a solid state drive (SSD), or an integrated circuit storage, for storing medical images. Specifically, the image storage apparatus 3 stores, as medical images, a radiotherapy planning CT image generated by the radiotherapy planning CT apparatus 1 and an MR image generated by the MRI integrated radiotherapy apparatus 6. The MR image is supplied to the machine learning apparatus 4.

The machine learning apparatus 4 is a computer including a processor such as a CPU, a memory such as a ROM or a RAM, a display, an input interface, and a communication interface. The machine learning apparatus 4 generates a trained model used by the irradiation control apparatus 5, based on the MR image generated by the MRI integrated radiotherapy apparatus 6. The trained model is supplied to the irradiation control apparatus 5.

The irradiation control apparatus 5 is a computer that controls irradiation by the MRI integrated radiotherapy apparatus 6, based on the radiotherapy plan, the MR image, and the trained model. The irradiation control apparatus 5 is implemented in a synchronizer for a radiotherapy apparatus, for example.

The MRI integrated radiotherapy apparatus 6 is an apparatus that irradiates a tumor or the like in the patient in accordance with a radiotherapy plan while monitoring the position of the tumor of the patient by MR imaging. The MRI integrated radiotherapy apparatus 6 is provided with an MR imaging mechanism 7, which is a mechanical device that performs MR imaging, and a radiotherapy mechanism 8, which is a mechanical device that performs radiotherapy.

Figure 2:
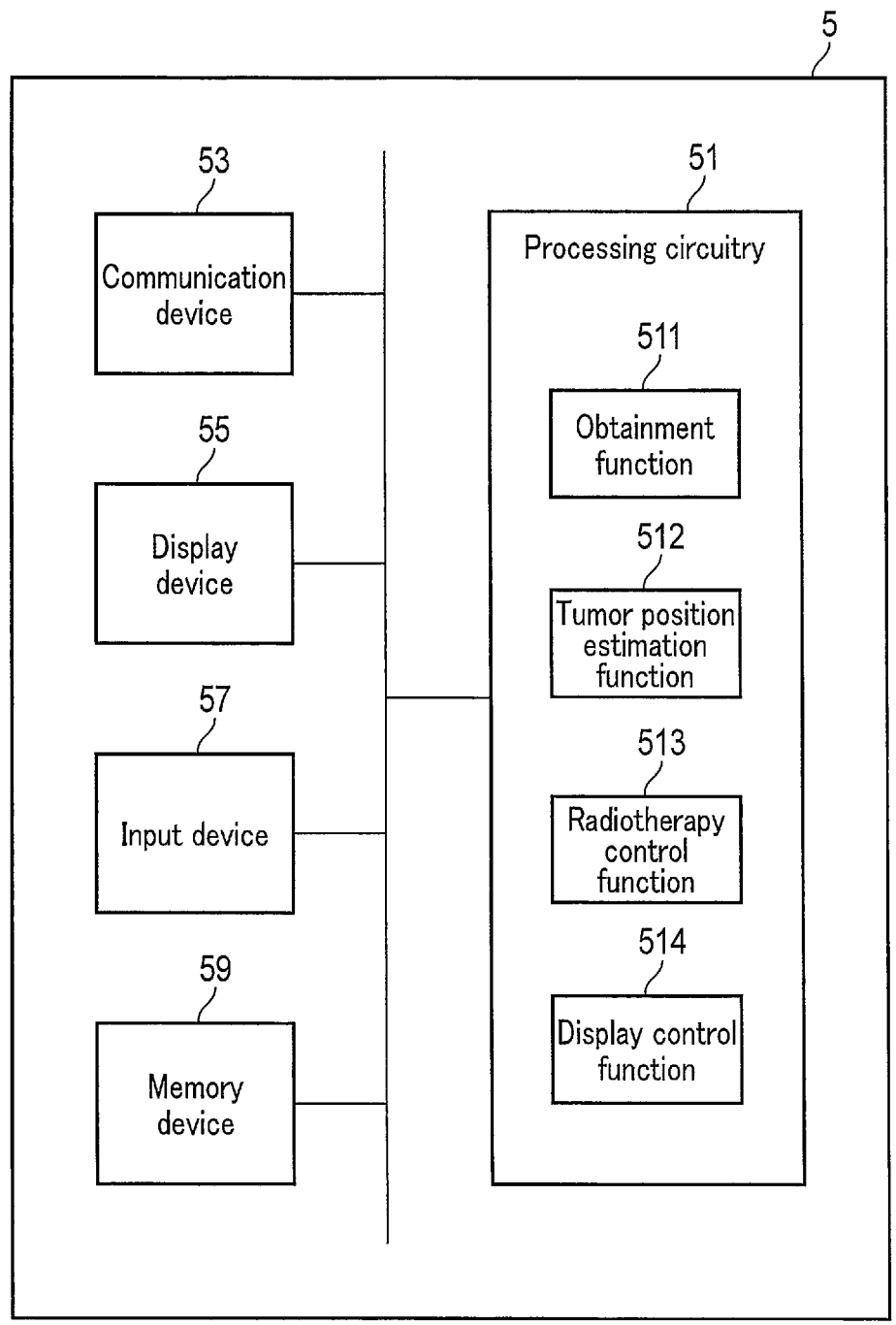
FIG. 2 shows a configuration example of an irradiation control apparatus in FIG. 1.

FIG. 2 shows a configuration example of the irradiation control apparatus 5. As shown in FIG. 2, the irradiation control apparatus 5 includes processing circuitry 51, a communication device 53, a display device 55, an input device 57, and a memory device 59.

The processing circuitry 51 includes a processor. The processor activates various programs installed in the memory device 59 or the like and thereby implements an obtainment function 511, a tumor position estimation function 512, a radiotherapy control function 513, and a display control function 514. Each of the functions 511 to 514 is not necessarily implemented by a single processing circuit 51. A plurality of independent processors may be combined into processing circuitry, and execute programs to implement the respective functions 511 to 514.

Through implementation of the obtainment function 511, the processing circuitry 51 obtains various types of information. Specifically, the processing circuitry 51 obtains a patient's radiotherapy plan generated by the radiotherapy planning apparatus 2, a trained model generated by the machine learning apparatus 4, and an MR image generated by the MRI integrated radiotherapy apparatus 6, and the like. Information need not necessarily have been directly obtained from the various apparatuses. Information received from the apparatuses may be stored in the memory device 59, and then obtained from the memory device 59.

Through implementation of the tumor position estimation function 512, the processing circuitry 51 inputs an MR image of a first time phase into the trained model and thereby estimates a position of a tumor region of the patient of a second time phase which is a predetermined time phase after the first time phase. Hereinafter, the position of the tumor region will be simply referred to as a "tumor position". The tumor position may be defined by a set of coordinates of a plurality of pixels constituting the tumor region included in the MR image, or may be defined by coordinates of a specific pixel. The tumor position may be defined by a distance and direction from an anatomical reference point included in the MR image to a reference point of the rumor region. The anatomical reference point may be set on an anatomical part, such as a bone, around the tumor region, which does not move due to body movement. The reference point of the tumor region may be a point closest to the anatomical reference point, or a center point, a barycenter point, or the like of the tumor region. Hereinafter, let us assume that the tumor position is defined by a set of coordinates of a plurality of pixels constituting the tumor region included in the MR image.

Through implementation of the radiotherapy control function 513, the processing circuitry 51 controls irradiation by the MRI integrated radiotherapy apparatus 6, based on the tumor position of the patient of the second time phase estimated by the tumor position estimation function 512.

Through implementation of the display control function 514, the processing circuitry 51 causes the display device 55 to display various types of information. For example, the processing circuitry 51 causes the tumor position of the second time phase to be displayed.

The communication device 53 is an interface for performing information communication via wire or radio with the radiotherapy planning CT apparatus 1, radiotherapy planning apparatus 2, image storage apparatus 3, machine learning apparatus 4, and MRI integrated radiotherapy apparatus 6 included in the radiotherapy system 100.

The display device 55 displays various types of information in accordance with the display control function 514 of the processing circuitry 51. As the display device 55, a liquid crystal display (LCD), a cathode ray tube (CRT) display, an organic electroluminescence display (OELD), a plasma display, or any other display may be used as appropriate. Alternatively, the display device 55 may be a projector.

The input device 57 receives various input operations from a user, converts a received input operation into an electrical signal, and outputs the electrical signal to the processing circuitry 51. Specifically, a mouse, a keyboard, a trackball, a switch, a button, a joy stick, a touch pad, a touch panel display, or the like is appropriately selected as the input device 57. The input device 57 may be a voice-input device using a voice signal from an input device, such as a microphone, which collects vocal sounds. The input device 57 may be non-contact input circuitry using an optical sensor. The input device 57 outputs to the processing circuitry 51 an electrical signal corresponding to an input operation on the input device. The input device 57 may be an input device provided in another computer connected via a network or the like.

The memory device 59 is a memory device, such as a ROM, a RAM, an HDD, an SSD, or an integrated circuit memory device, which stores various types of information. The memory device 59 stores, for example, an MR image, a radiotherapy plan, a trained model, and the like obtained by the obtainment function 511. Instead of being the above-described memory device, the memory device 59 may be a driver that writes and reads various types of information to and from a semiconductor memory device or a portable storage medium such as a compact disc (CD), a digital versatile disc (DVD), a flash memory, or the like. The memory device 59 may be provided in another computer connected to the irradiation control apparatus 5 via wire or radio.

Figure 3:
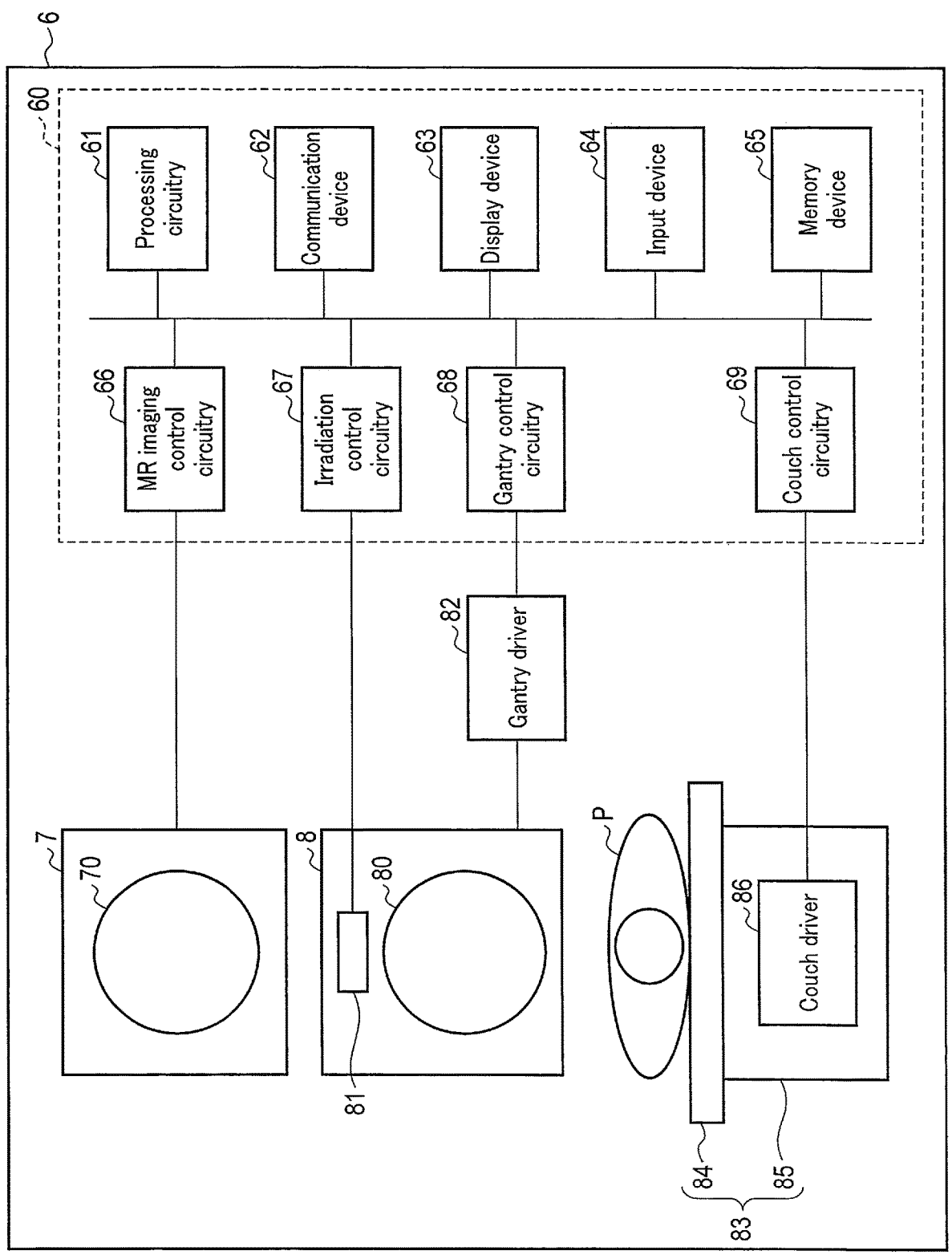
FIG. 3 is a diagram showing a configuration example of an MRI integrated radiotherapy apparatus in FIG. 1.

FIG. 3 is a diagram showing a configuration example of the MRI integrated radiotherapy apparatus 6. As shown in FIG. 3, the MRI integrated radiotherapy apparatus 6 includes the MR imaging mechanism 7, the radiotherapy mechanism 8, and a console 60.

The MR imaging mechanism 7 and the radiotherapy mechanism 8 form one gantry, and share one couch 83. For example, the MR imaging mechanism 7 and the radiotherapy mechanism 8 include bores 70 and 80, respectively, and the gantry has a cylindrical shape including the bores 70 and 80. The MR imaging mechanism 7 and the radiotherapy mechanism 8 are arranged so that the bore 70 and the bore 80 communicate with each other. A top plate 84 of the couch 83 is inserted into the bores 70 and 80.

The MR imaging mechanism 7 includes, for example, a static magnetic field magnet, a gradient magnetic field power supply, a gradient magnetic field coil, transmission circuitry, a transmitter coil, a receiver coil, and reception circuitry. The MR imaging mechanism 7 controls the gradient magnetic field power supply, the transmission circuitry, the reception circuitry, and the like in accordance with a command from MR imaging control circuitry 66, and performs MR imaging on a patient. In the MR imaging, under application of a static magnetic field by way of a static magnetic field magnet, application of a gradient magnetic field by way of the gradient magnetic field coil and application of RF pulses by way of the transmitter coil are repeated. An MR signal from a patient P is released in response to the application of the RF pulses. The released MR signal is received through the receiver coil. The received MR signal is subjected to signal processing, such as A/D conversion, by the reception circuitry. The A/D converted MR signal is referred to as k-space data. The k-space data is supplied to the MR imaging control circuitry 66.

The radiotherapy mechanism 8 rotatably supports an irradiator 81. The irradiator 81 emits radiation in accordance with a command from irradiation control circuitry 67. As the radiation, any type of radiation used for radiotherapy, such as X rays, gamma rays, or particle rays, may be used. A gantry driver 82 is embedded in the radiotherapy mechanism 8. The gantry driver 82 rotates the irradiator 81 about the rotation axis in accordance with a command from gantry control circuitry 68.

The couch 83 includes a top plate 84, a base 85, and a couch driver 86. The patient P is placed on the top plate 84. The top plate 84 is movably supported by the base 85. The base 85 is placed on a floor. The couch driver 86 is embedded in the base 85. The couch driver 86 moves the top plate 84 in accordance with a command from couch control circuitry 69.

As shown in FIG. 3, the console 60 includes processing circuitry 61, a communication device 62, a display device 63, an input device 64, a memory device 65, MR imaging control circuitry 66, irradiation control circuitry 67, gantry control circuitry 68, and couch control circuitry 69.

The processing circuitry 61 includes a processor. The processing circuitry 61 activates various programs installed in the memory device 59 or the like and thereby controls the communication device 62, the display device 63, the input device 64, the memory device 65, the MR imaging control circuitry 66, the irradiation control circuitry 67, the gantry control circuitry 68, and the couch control circuitry 69.

The communication device 62 is an interface for performing information communication via wire or radio with the radiotherapy planning CT apparatus 1, radiotherapy planning apparatus 2, image storage apparatus 3, machine learning apparatus 4, and irradiation control apparatus 5 included in the radiotherapy system 100.

The display device 63 displays various types of information in accordance with control by the processing circuitry 61. As the display device 63, an LCD, a CRT display, an OELD, a plasma display, or any other display may be used as appropriate. The display device 63 may be a projector.

The input device 64 receives various input operations from a user, converts a received input operation into an electrical signal, and outputs the electrical signal to the processing circuitry 61. Specifically, a mouse, a keyboard, a trackball, a switch, a button, a joy stick, a touch pad, a touch panel display, or the like is appropriately selected as the input device 64. The input device 64 may be a voice-input device using a voice signal from an input device, such as a microphone, which collects vocal sounds. The input device 64 may be non-contact input circuitry using an optical sensor. The input device 64 outputs to the processing circuitry 61 an electrical signal corresponding to an input operation on the input device. The input device 64 may be an input device provided in another computer connected via a network or the like.

The memory device 65 is a memory device, such as a ROM, a RAM, an HDD, an SSD, or an integrated circuit memory device, which stores various types of information. The memory device 65 stores, for example, an MR image, a radiotherapy plan, and the like. Instead of being the above-described memory device, the memory device 65 may be a driver that writes and reads various types of information to and from a semiconductor memory device, a portable storage medium such as a CD, a DVD, or a flash memory, or the like. The memory device 65 may be provided in another computer connected to the irradiation control apparatus 5 via wire or radio.

The MR imaging control circuitry 66 includes, as hardware resources, a processor such as a CPU, and a memory such as a ROM or a RAM. The MR imaging control circuitry 66 synchronously controls the gradient magnetic field power supply, transmission circuitry, and reception circuitry on the basis of a preset MR imaging condition, executes MR imaging on the patient P in accordance with a pulse sequence corresponding to the MR imaging condition, and collects k-space data regarding the patient P. The MR imaging control circuitry 66 reconstructs an MR image of the patient P based on the collected k-space data. The MR image is stored in the memory device 65.

The irradiation control circuitry 67 includes, as hardware resources, a processor such as a CPU, and a memory such as a ROM or a RAM. The irradiation control circuitry 67 controls the irradiator 81 to emit radiation in accordance with a radiotherapy plan received from the radiotherapy planning apparatus 2. The irradiation control circuitry 67 switches the irradiation on and off in accordance with control by the radiotherapy control function 513 of the irradiation control apparatus 5.

The gantry control circuitry 68 includes, as hardware resources, a processor such as a CPU, and a memory such as a ROM or a RAM. The gantry control circuitry 68 controls the gantry driver 82 to emit radiation from an irradiation angle included in the radiotherapy plan. The irradiation angle may be input by a user via the input device 64.

The couch control circuitry 69 includes, as hardware resources, a processor such as a CPU, and a memory such as a ROM or a RAM. The couch control circuitry 69 controls the couch driver 86 to move the top plate 84 to a given position. The couch control circuitry 69 also moves the top plate 84 in accordance with control by the radiotherapy control function 513 of the irradiation control apparatus 5. The position of the top plate 84 may be input by a user via the input device 64.

Next, details of the processing of the radiotherapy system 100 according to the present embodiment will be described.

As described above, through implementation of the tumor position estimation function 512, the processing circuitry 51 of the irradiation control apparatus 5 inputs an MR image of a first time phase to the trained model and thereby estimates a position of a tumor region of the patient of a second time phase which is a predetermined time phase after the first time phase. The first time phase represents a time of acquiring or generating an MR image to be processed. The time phase may be defined by a phase of a biological waveform of a patient, or a time. Typically, the MR image of the first time phase is an MR image of the latest frame of MR images collected by dynamic imaging; therefore, the first time phase will be referred to as a "present time phase". The second time phase is set to a time phase that is a predetermined time phase after the first time phase, and thus will be referred to as a "future time phase".

Let us assume that the trained model according to the present embodiment is a neural network with a multi-layer architecture including two or more layers. The neural network includes a composite function with parameters, which is defined by a combination of a plurality of adjustable functions and parameters. A weighting coefficient and a bias are collectively called a "parameter".

Figure 4:
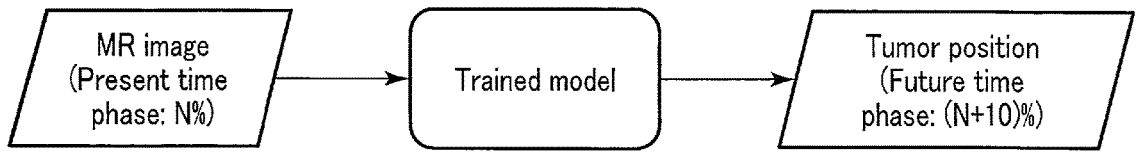
FIG. 4 is a diagram schematically showing an input and output of a trained model according to the present embodiment.

FIG. 4 is a diagram schematically showing an input and output of the trained model according to the present embodiment. As shown in FIG. 4, the trained model is a neural network trained to, in response to an input of an MR image of a present time phase, output a tumor position of a future time phase, which is a predetermined time phase after the present time phase. For example, when the present time phase is N %, the future time phase is set to (N+10)%, which is 10% after the present time phase N %. In the present embodiment, the present time phase is expressed as N % (where N is a given time phase value from 1 to 100) when one cycle of the respiratory waveform is expressed as 100%. The tumor position of the future time phase may be output as a sequence of image coordinates of the pixels of the tumor region, as image data in which the tumor region is rendered, or as a sequence of real coordinates of the pixels of the tumor region. The output form is not limited to the above, and the tumor position of the future time phase may be output in any form as long as it can be recognized.

The time phase difference (predetermined time phase) of 10% between the present time phase N % and the future time phase (N+10)% may be set to a time shorter than the frame rate of MR imaging by the MRI integrated radiotherapy apparatus 6. Use of the trained model according to the present embodiment enables estimation of the tumor position of the future time phase (N+10)% from the MR image of the present time phase N %. That is, the tumor position can be estimated with a temporal resolution finer than the frame rate. Hereinafter, the time phase difference will be referred to as a "time phase lag". The case where the time phase lag is 10% will be described as an example; however, the present embodiment is not limited to this, and the time phase lag may be any time shorter than the frame rate. For example, the time phase lag may be approximately from 0.1 to 2.0 seconds if converted into time.

Specifically, the time phase lag may be set to a value larger than the time difference between a reference time of the MR image to a time when irradiation control is performed and smaller than the time interval corresponding to the frame rate. This is because, if the time phase lag is shorter than the time difference, the tumor position of the future time phase output by the trained model is already a past tumor position at the time of irradiation control. The reference time of the MR image may be set to a time when data corresponding to the k-space low frequency region of the MR image is collected, a time when data corresponding to the entire k-space region is collected, or another time.

Figure 5:
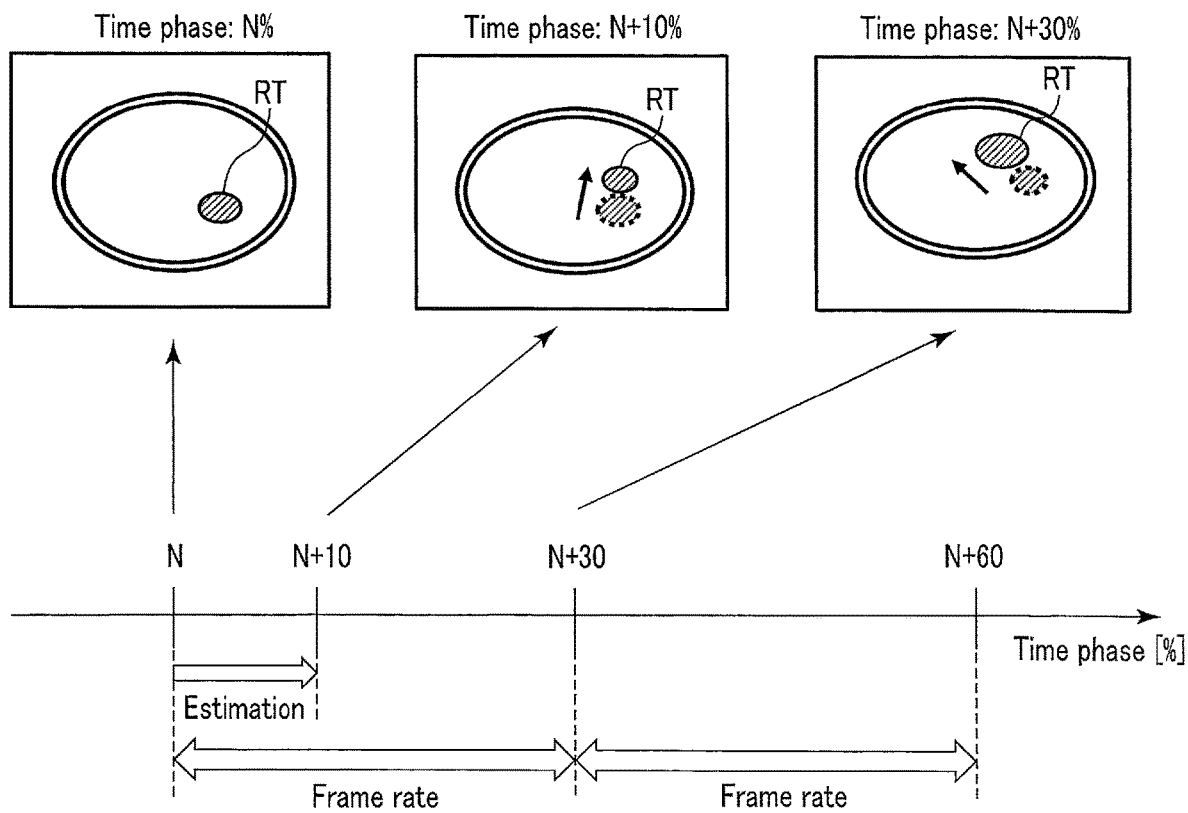
FIG. 5 is a schematic diagram showing variability of the tumor position over time.

FIG. 5 is a schematic diagram showing variability of the tumor position over time. The upper part of FIG. 5 schematically shows MR images, and the lower part of FIG. 5 shows a timeline of time phases. As shown in FIG. 5, the time-series MR images are collected by the MRI integrated radiotherapy apparatus 6 at a frame rate of 30%. Since a patient, who is a subject of the MRI integrated radiotherapy apparatus 6, has a tumor, a tumor region RT is rendered in the MR image of each time phase. Let us assume the position of the tumor region RT changes due to a body movement such as a respiration of the patient. In other words, let us assume that the tumor region RT occurs in a position affected by body movement.

The frame rate of MR imaging of the MRI integrated radiotherapy apparatus 6 is expected to be relatively low. The frame rate is set to, for example, 30% as shown in FIG. 5. In this case, it is not possible to obtain an accurate tumor position of each time phase from N % to (N+30)% from an MR image collected by the MRI integrated radiotherapy apparatus 6. The MRI integrated radiotherapy apparatus 6 performs MR imaging on a patient, identifies a position of a tumor by image processing, and controls irradiation in accordance with the position of the tumor, during irradiation. However, the image processing requires time; therefore, the actual tumor position may have moved out of the irradiation range when irradiation control is performed.

Use of the trained model shown in FIG. 4 enables estimation of the tumor position of the future time phase (N+10)% from the MR image of the present time phase N %. The future time phase is not limited to the time phase that is 10% after the present time phase, and may be set to any time phase after the present time phase and before a time phase that is a time phase lag after the present time phase.

Next, generation of a trained model by the machine learning apparatus 4 will be described.

FIG. 6 is a schematic diagram of processing for generating a trained model by the machine learning apparatus 4. As shown in FIG. 6, the machine learning apparatus 4 generates a trained model by training an untrained model based on a plurality of training samples. The untrained model is a neural network in which parameters are set to initial values. Each training sample is constituted by a combination of input data and truth data. As the input data, an MR image of a first time phase (also referred to as an "input MR image") is used. As the truth data, a tumor position of a second time phase (also referred to as a "truth tumor position") is used. For example, the first time phase is No corresponding to a present time phase, and the second time phase is (N+10)% corresponding to a future time phase. The tumor position of the future time phase is identified from actual MR images of future time phases generated by the MRI integrated radiotherapy apparatus 6 performing MR imaging on a patient.

Specifically, for collection of training samples, the MRI integrated radiotherapy apparatus 6 generates time-series MR images by performing dynamic imaging on a subject, such as a patient, at a predetermined frame rate. The time-series MR images are supplied to the machine learning apparatus 4. The machine learning apparatus 4 specifies a combination of an MR image of a given reference time phase and an MR image of a time phase that is a time phase lag after the reference time phase (hereinafter referred to as "another time phase") from the time-series MR images. For example, a combination of an MR image of a reference time phase 0% and an MR image of another time phase 30%, a combination of an MR image of a reference time phase 30% and an MR image of another time phase 60%, and a combination of an MR image of a reference time phase 60% and an MR image of another time phase 90% are specified. That is, the reference time phase of an MR image used for training need not be the same for all training samples, and may vary between training samples.

For each training sample, the machine learning apparatus 4 performs given region extraction processing, such as threshold processing, machine learning, or image recognition, on the MR image of another time phase, and identifies a tumor position. The machine learning apparatus 4 may identify a region designated by the user as the tumor region. Flags indicating affiliation to the same training sample are assigned respectively to the MR image of the reference time phase and the tumor position of another time phase. The training samples are stored in the machine learning apparatus 4.

As mentioned above, the frame rate of the MR imaging of the MRI integrated radiotherapy apparatus 6 is expected to be relatively low.

Figure 7:
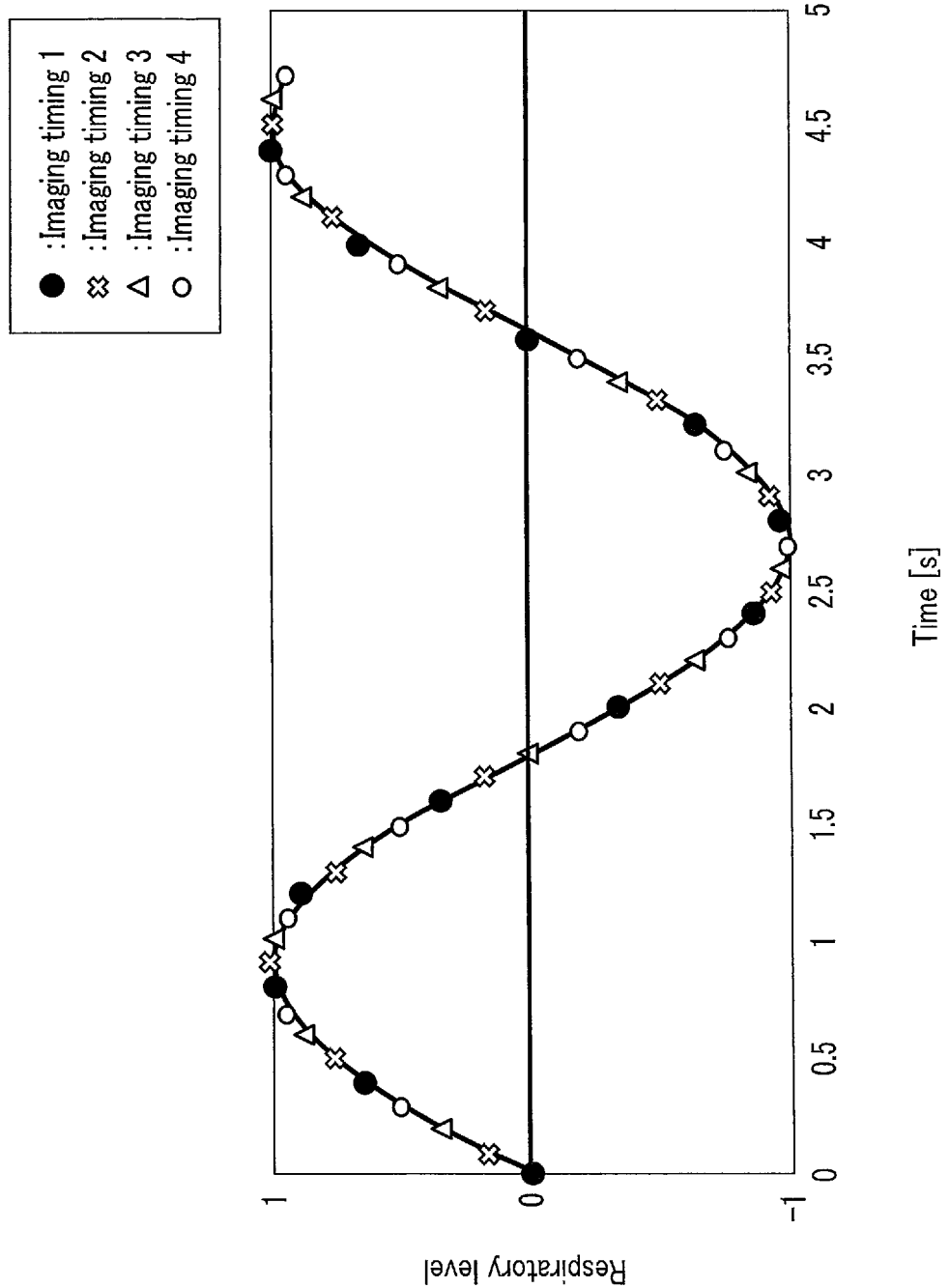
FIG. 7 is a diagram showing a relationship between imaging timing and time phases of MR images.

FIG. 7 is a diagram showing a relationship between imaging timing and time phases of MR images. Marks indicating time phases of MR image collection of respective types of imaging timing are shown on a respiratory waveform. As shown in FIG. 7, if one respiratory cycle is 3.6 seconds for example, only about ten training samples can be acquired by one type of imaging timing. To densely collect training samples in one respiratory cycle of a patient, the MRI integrated radiotherapy apparatus 6 performs dynamic imaging at different types of imaging timing with respect to one respiratory cycle. Specifically, the MRI integrated radiotherapy apparatus 6 performs multiple times of dynamic imaging by shifting imaging timing, while the patient repeatedly respires. For example, the first dynamic imaging is performed at imaging timing 1, and the second dynamic imaging is performed at imaging timing 2, the time phases of which are shifted from the time phases of imaging timing 1 by a predetermined time phase. Dynamic imaging is repeatedly performed by shifting imaging timing until training samples are densely collected with respect to one respiratory cycle.

The training samples need not be all the same patient's, and may be various patients'. The time phase lag between input data and truth data is desirably the same for all training samples, but may vary thereamong as long as it is within a tolerable range. All training samples need not be collected by the MRI integrated radiotherapy apparatus 6, and some or all training samples may be collected by another MRI integrated radiotherapy apparatus or an unintegrated MRI apparatus.

Upon collection of a plurality of training samples, the machine learning apparatus 4 trains an untrained neural network based on the training samples. Specifically, the machine learning apparatus 4 inputs an input MR image to the untrained model and performs forwardpropagation, thereby outputting an estimated tumor position. Next, the machine learning apparatus 4 inputs a difference (error) between the estimated tumor position and the truth tumor position to the untrained model and performs backpropagation, thereby calculating a gradient vector. Next, the machine learning apparatus 4 updates parameters, such as a weight and a bias, of the untrained model based on the gradient vector. A trained model is completed by repeating the forwardpropagation and backpropagation for a number of training samples and updating the parameters. The trained model is supplied to the irradiation control apparatus 5.

The machine learning apparatus 4 is described above as being configured to input an MR image to a neural network as input data in order to perform training. However, the present embodiment is not limited to this. For example, the machine learning apparatus 4 may input an MR image and an evaluation result of a tumor position serving as truth data to a neural network as input data. The evaluation result of the tumor position is a result of accuracy evaluation on identification of the tumor position. For example, when a tumor region is identified by image processing, the tumor region may not be accurately identified. In this case, the user evaluates, through visual observation or the like, the accuracy of identification of the tumor region performed by image processing, and attaches the evaluation result to the tumor position. The evaluation result may be an evaluation with two rating scales, such as good and no good, an evaluation with three rating scales, such as excellent, good, and fair, or an evaluation with more rating scales. When the user manually identifies the tumor region, the evaluation result may also be used as input data. Accordingly, a neural network can be trained in consideration of the evaluation result of the tumor position, and the accuracy of tumor position estimation is improved.

Next, irradiation by the irradiation control apparatus 5 will be described.

Figure 8:
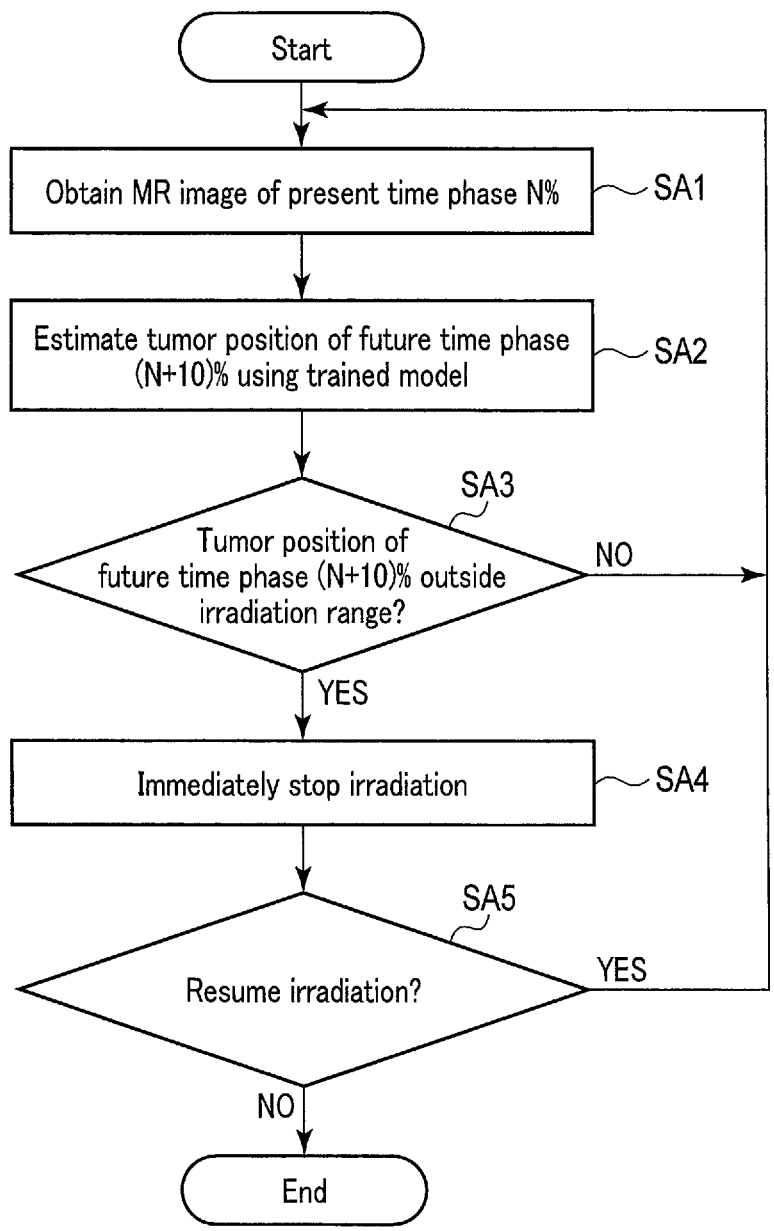
FIG. 8 is a diagram showing an example of the flow of irradiation control by an irradiation control apparatus in FIG. 2.

FIG. 8 is a diagram showing an example of the flow of irradiation control by the irradiation control apparatus 5. The irradiation control shown in FIG. 8 is performed in parallel with radiotherapy by the MRI integrated radiotherapy apparatus 6. In radiotherapy, the patient P is placed on the top plate 84, and the patient P and top plate 84 are positioned so that the tumor region is positioned within an irradiation range set in the radiotherapy plan. The irradiation range of the patient P positioned at the aforementioned position is irradiated by the radiotherapy mechanism 8. Let us assume that the MR imaging mechanism 7 is configured to perform MR imaging on the patient P positioned at the aforementioned position. For example, a pair of MR imaging mechanisms 7 are arranged in such a manner as to interpose the radiotherapy mechanism 8 from both longitudinal sides of the top plate 84. In parallel with radiotherapy by the radiotherapy mechanism 8, dynamic imaging is executed by the MR imaging mechanisms 7 at a predetermined frame rate, and time-series MR images are reconstructed by the MR imaging control circuitry 66. The latest MR image of the time-series MR images is transmitted to the irradiation control apparatus 5 in real time. Let us assume that the tumor region of the patient is rendered in each MR image. To monitor the respiratory movement of the patient P, a respiratory waveform is collected by a respiratory sensor, and is transmitted to the irradiation control apparatus 5.

As shown in FIG. 8, through implementation of the obtainment function 511, the processing circuitry 51 of the irradiation control apparatus 5 obtains an MR image of the present time phase N %, which includes the tumor region of the patient P (step SA1). The MR image of the present time phase N % is an MR image of the latest time phase of the time-series MR images generated by the MRI integrated radiotherapy apparatus 6 performing MR imaging on the patient P.

After step SA1, through implementation of the tumor position estimation function 512, the processing circuitry 51 estimates the tumor position of the future time phase (N+10)% using the trained model (step SA2). In step SA2, the processing circuitry 51 inputs the MR image of the present time phase N % obtained in step SA1 to the trained model generated by the machine learning apparatus 4 and thereby estimates the tumor position of the future time phase (N+10)%.

As described above, the time phase lag of 10% from the present time phase N %, i.e., the future time phase (N+10)% to be predicted, may be set to a value larger than the time difference between the reference time of the MR image and the time when irradiation control is performed and smaller than the time interval corresponding to the frame rate. Here, the time when irradiation control is performed is preferably a time when the irradiation control circuitry 67 starts irradiation stop control on the irradiator 81, not the time when irradiation from the irradiator 81 actually stops.

After step SA2, through implementation of the radiotherapy control function 513, the processing circuitry 51 determines whether or not the tumor position of the future time phase (N+10)% is outside the irradiation range (step SA3). When it is determined that the tumor position of the future time phase (N+10)% is not outside the irradiation range (NO in step SA3), the processing circuitry 51 proceeds to step SA1, obtains an MR image of the next present time phase N %, and repeats steps SA1 to SA3.

Figure 9:
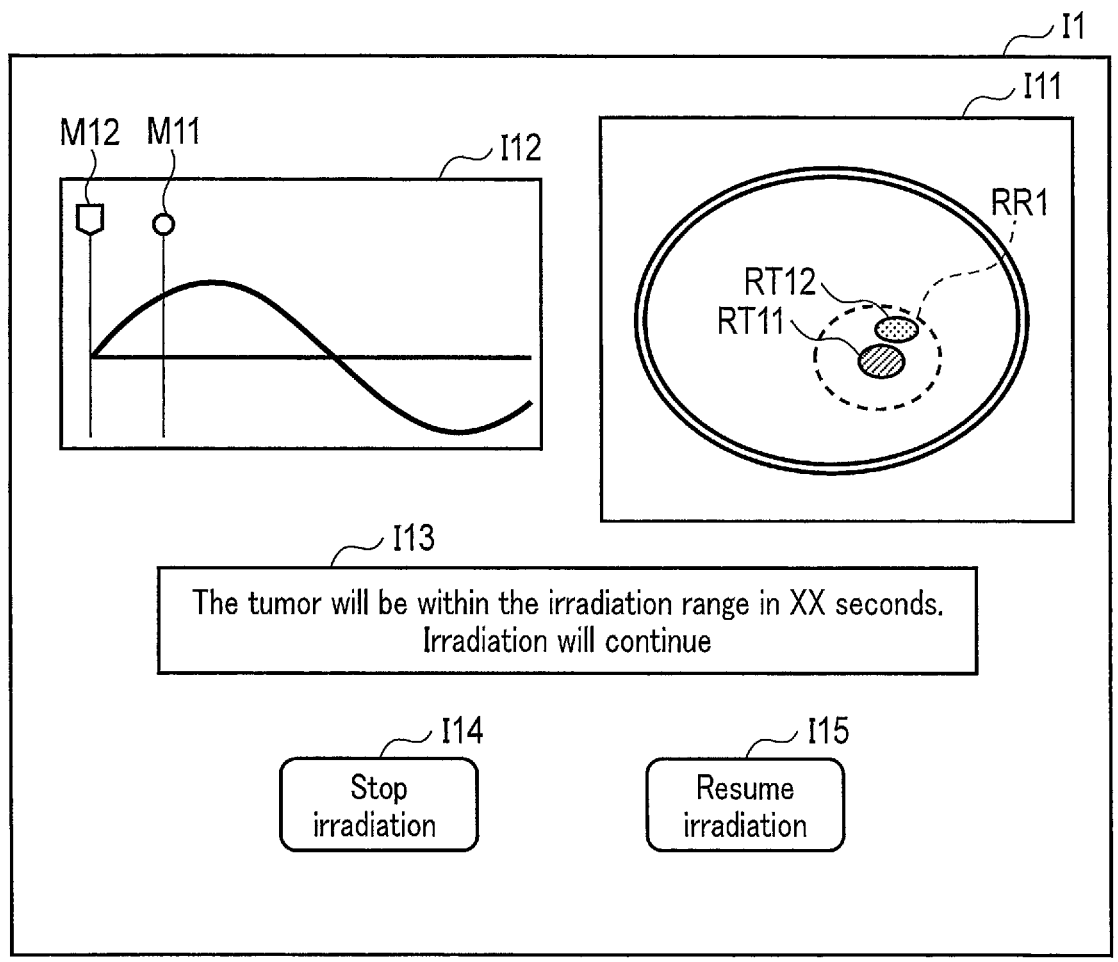
FIG. 9 is a diagram showing an example of a display screen in the case of NO in step SA3.

FIG. 9 is a diagram showing an example of a display screen (irradiation continuation pattern) I1 in the case of NO in step SA3. As shown in FIG. 9, the display screen I1 shows an MR image I11, a respiratory waveform I2, a message I13, an irradiation stop icon I14, and an irradiation resume icon I15. As the MR image I11, for example the MR image of the present time phase No obtained in step SA1 is displayed. On the MR image I11, a tumor position RT11 of the present time phase N % is highlighted with color or the like. A tumor position RT12 of the future time phase (N+10)% estimated in step SA2 is also displayed on the MR image I11. The tumor position RT12 of the future time phase (N+10)% is also highlighted with color or the like. As described above, the highlighting of the tumor position RT11 of the present time phase N % and the tumor position RT12 of the future time phase (N+10)% on the MR image I11 of the present time phase N % enables the user to clearly ascertain the positional relationship between the tumor positions RT11 and RT12.

As shown in FIG. 9, the irradiation range RR1 may be displayed on the MR image I11. The irradiation range RR1 may be, for example, the one set as one parameter of the radiotherapy condition of the radiotherapy plan. As described above, the display of the tumor position RT11 of the present time phase N %, the tumor position RT12 of the future time phase (N+10)%, and the irradiation range RR1 enables the user to clearly ascertain the positional relationship of the tumor position RT11 of the present time phase N % and the tumor position RT12 of the future time phase (N+10)% with the irradiation range RR1.

In FIG. 9, the tumor position RT12 of the future time phase (N+10)% is within the irradiation range RR1; therefore, it is determined that the tumor position RT12 of the future time phase (N+10)% is not outside the irradiation range RR1. In this case, a message I13 to that effect is displayed as shown in FIG. 9. For example, a message such as "The tumor will be within the irradiation range in XX seconds. Irradiation will continue." is displayed. In the case of irradiation continuation, the irradiation stop icon 114 may be displayed in a color, shape, text, or the like that indicates irradiation continuation in order to clearly inform the user that irradiation will continue.

It is possible to determine that the tumor position RT12 is outside the irradiation range RR1 when the entire tumor position RT12 is outside the irradiation range RR1, when part of the tumor position RT12 is outside the irradiation range RR1, or when a predetermined ratio or a specific portion of the tumor position RT12 is outside the irradiation range RR1. The determination criteria can be discretionarily set.

As shown in FIG. 9, the respiratory waveform I12 of the patient may be displayed on the display screen I1. The respiratory waveform I12 may be measured in real time by the respiratory sensor or the like, and displayed. For example, the latest respiratory time phase is displayed in real time so that the respiratory waveform flows from left to right with time. A mark M11 representing the present time phase N. and a mark M12 representing the future time phase (N+10)% may be displayed on the respiratory waveform I12. This enables the user to clearly ascertain the relationship between the tumor positions RT11, RT12, the present time phase N %, and the future time phase (N+10)%.

When it is determined that the tumor position of the future time phase (N+10)% is outside the irradiation range in step SA3 (YES in step SA3), the processing circuitry 51 immediately stops the irradiation through implementation of the radiotherapy control function 513 (step SA4).

Figure 10:
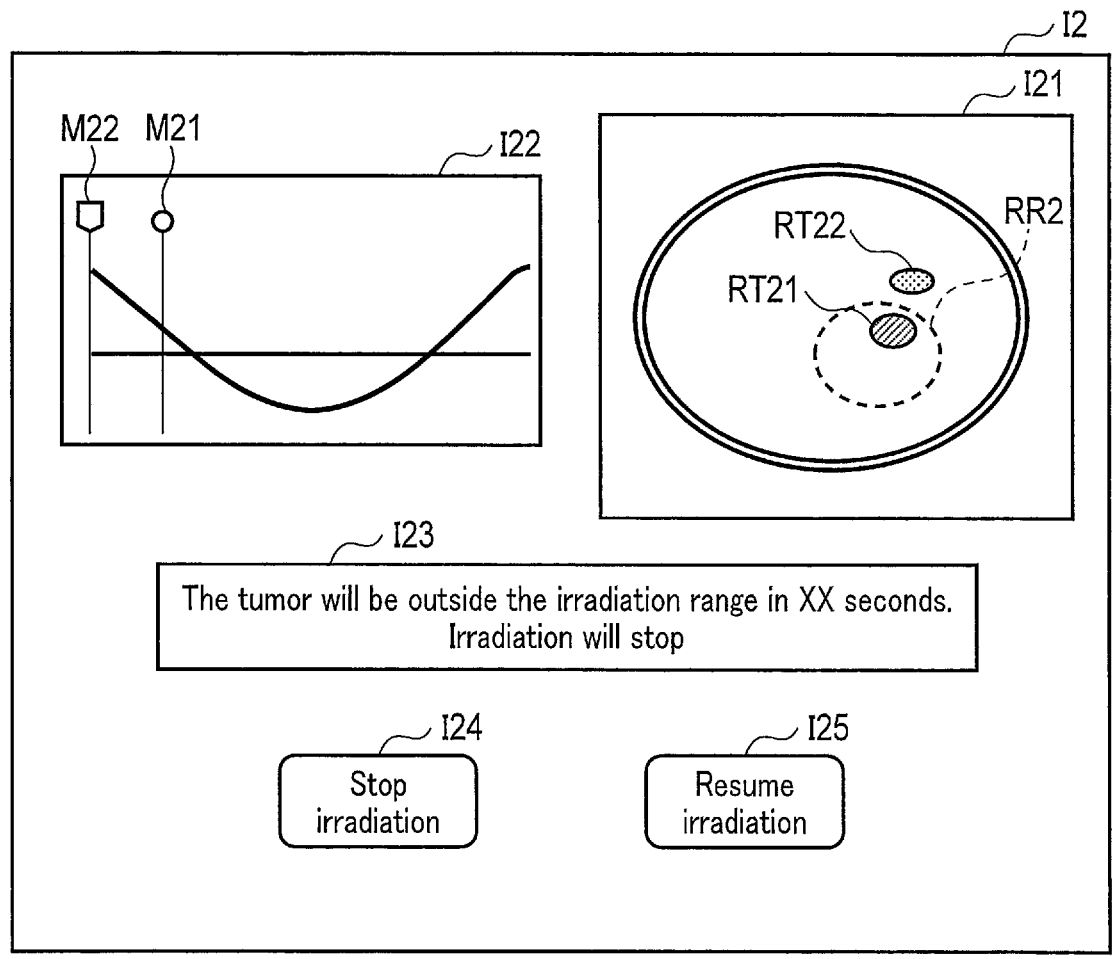
FIG. 10 is a diagram showing an example of a display screen (irradiation stop pattern) in the case of YES in step SA3.

FIG. 10 is a diagram showing an example of a display screen (irradiation stop pattern) 12 in the case of YES in step SA3. Like the display screen I1 in FIG. 9, the display screen I2 shows an MR image 121, a respiratory waveform I22, a message I23, an irradiation stop icon 124, and an irradiation resume icon I25, as shown in FIG. 10. As the MR image 121, an MR image of the present time phase N % as well as a tumor position RT21 of the present time phase N %, a tumor position RT22 of the future time phase (N+10)%, and an irradiation range RR2 are displayed, like the MR image I11 in the display I1 in FIG. 9. In FIG. 10, the entire tumor position RT22 of the future time phase (N+10)% is outside the irradiation range RR2; therefore, it is determined that the tumor position of the future time phase (N+10)% is outside the irradiation range. In this case, a message I23 to that effect is displayed as shown in FIG. 10. For example, a message such as "The tumor will be outside the irradiation range within XX seconds. Irradiation will stop." is displayed. In the case of irradiation stoppage, the irradiation stop icon 124 may be displayed in a color, shape, text, or the like that indicates irradiation stoppage in order to clearly inform the user that irradiation will stop.

When it is determined that the tumor position of the future time phase (N+10)% is outside the irradiation range, the processing circuitry 51 supplies the MRI integrated radiotherapy apparatus 6 with an irradiation stop command through implementation of the radiotherapy control function 513. Upon receipt of the irradiation stop command, the processing circuitry 61 of the MRI integrated radiotherapy apparatus 6 operates the irradiation control circuitry 67. The irradiation control circuitry 67 controls the irradiator 81 and thereby immediately stops the irradiation. Accordingly, the irradiation can be stopped before the actual respiratory time phase reaches the future time phase, and radiation exposure of the normal region in the irradiation range RR2 can be suppressed.

The irradiation is described as automatically being stopped when it is determined that the tumor position of the future time phase (N+10)% is outside the irradiation range in step S4; however, the present embodiment is not limited to this. For example, when the user judges that the tumor position of the future time phase (N+10)% is outside the irradiation range, the user presses the irradiation stop icon 124, which is shown in FIG. 10, through the input device 57. In response to the pressing of the irradiation stop icon 124, the processing circuitry 51 supplies the MRI integrated radiotherapy apparatus 6 with an irradiation stop command through implementation of the radiotherapy control function 513. Upon receipt of the irradiation stop command, the processing circuitry 61 of the MRI integrated radiotherapy apparatus 6 operates the irradiation control circuitry 67, and the irradiation control circuitry 67 controls the irradiator 81 and thereby stops the irradiation.

In the display examples of FIGS. 9 and 10, the time phase lag between the present time phase N % and the future time phase (N+10)% is expressed in seconds as in the messages 113 and 123, but may be expressed as a time phase.

In step SA4, the processing circuitry 51 determines whether or not to resume irradiation through implementation of the radiotherapy control function 513 (step SA5). In step SA5, the processing circuitry 51 waits for the irradiation resume icon I25 in FIG. 10 to be pressed through the input device 57. When the irradiation resume icon I25 is pressed, the processing circuitry 51 determines that irradiation be resumed.

When it is determined that irradiation be resumed in step SA5 (YES in step SA5), the processing circuitry 51 supplies the MRI integrated radiotherapy apparatus 6 with an irradiation resume command through implementation of the radiotherapy control function 513. Upon receipt of the irradiation resume command, the processing circuitry 61 of the MRI integrated radiotherapy apparatus 6 operates the irradiation control circuitry 67, and the irradiation control circuitry 67 controls the irradiator 81 and thereby resumes irradiation.

The processing circuitry 51 then proceeds to step SA1, obtains an MR image of the next present time phase N %, and repeats steps SA1 to SA5. When it is determined that irradiation not be resumed in step SA5 (NO is step SA5) or when a predetermined termination condition is satisfied, the processing circuitry 51 terminates the irradiation control shown in FIG. 8. The predetermined termination condition is a completion of irradiation of one day's dose, for example.

This is the end of the description of the irradiation control shown in FIG. 8.

The irradiation control shown in FIG. 8 is an example, and can be modified in various ways. For example, a tumor position of one future time phase is estimated in step SA2 in the above case. However, the present embodiment is not limited to this. For example, a trained model may be prepared for each of a plurality of future time phases. In this case, the processing circuitry 51 may input the MR image of the present time phase N % obtained in step SA1 to each trained model and thereby estimate a plurality of tumor positions of the future time phases.

As another example, the processing circuitry 51 may determine in step SA5 whether or not to resume irradiation automatically, instead of using a pressing of the irradiation resume icon 125 as a trigger.

FIG. 11 is a diagram showing another example of the flow of irradiation control by the irradiation control apparatus 5. Let us assume that irradiation has been stopped by step SA4 in FIG. 8 when the flow of FIG. 11 starts.

As shown in FIG. 11, the processing circuitry 51 of the irradiation control apparatus 5 obtains an MR image of a present time phase No through implementation of the obtainment function 511 (step SB1). The MR image of the present time phase N % is an image of one or more frames after the time phase of the MR image obtained in step SA1 of FIG. 8.

After step SB1, through implementation of the tumor position estimation function 512, the processing circuitry 51 estimates a tumor position of a future time phase (N+10)% using the trained model (step SB2). The processing in step SB2 is similar to that in step SA2.

As described above, the time phase lag of 10% from the present time phase N %, i.e., the future time phase (N+10)% to be predicted, may be set to a value larger than the time difference between a reference time of the MR image and a time when irradiation control is performed and smaller than the time interval corresponding to the frame rate. The time when irradiation control is performed is the time when irradiation is actually performed. That is, the time when irradiation control is performed is preferably the time when irradiation is actually performed by the irradiator 81, not the time when the irradiation control circuitry 67 starts irradiation control on the irradiator 81. Accordingly, the possibility that the tumor position will be outside the irradiation range at the time when irradiation is actually performed can be lowered.

After step SB2, the processing circuitry 51 determines whether or not the tumor position of the future time phase (N+10)% is included in the irradiation range through implementation of the radiotherapy control function 513 (step SB3). When it is determined that the tumor position of the future time phase (N+10)% is not included in the irradiation range (NO in step SB3), the processing circuitry 51 proceeds to step SB1, obtains an MR image of the next present time phase N %, and repeats steps SB1 to SB3.

The processing for determining whether or not the tumor position of the future time phase (N+10)% is included in the irradiation range in step SB3 is similar to the determination processing in step SA3. It is possible to determine that the tumor position is included in the irradiation range when the entire tumor position is included in the irradiation range, when part of the tumor position is included in the irradiation range, or when a predetermined ratio or a specific portion of the tumor position is included in the irradiation range. The determination criteria can be discretionarily set.

When it is determined that the tumor position of the future time phase (N+10)% is included in the irradiation range in step SB3 (YES in step SB3), the processing circuitry 51 supplies the MRI integrated radiotherapy apparatus 6 with an irradiation resume command through implementation of the radiotherapy control function 513. Upon receipt of the irradiation resume command, the processing circuitry 61 of the MRI integrated radiotherapy apparatus 6 operates the irradiation control circuitry 67, and the irradiation control circuitry 67 controls the irradiator 81 and thereby resumes irradiation (step SB4). Upon resumption of irradiation, the processing circuitry 51 performs the irradiation control shown in FIG. 8. The radiotherapy is terminated in response to completion of irradiation of one day's dose, for example.

This is the end of the description of the irradiation control shown in FIG. 11.

In the above description, the irradiation is described as being stopped when it is determined that the tumor position of the future time phase is outside the irradiation range. However, the present embodiment is not limited to this. The processing circuitry 51 may control the position of the top plate 84 based on the tumor position of the future time phase. For example, the processing circuitry 51 moves the top plate 84 on which the patient is placed, so that the tumor position of the future time phase is included in the irradiation range. Specifically, the processing circuitry 51 calculates a deviation of the tumor position of the future time phase from the irradiation range. For example, the processing circuitry 51 calculates a deviation of a reference position (such as a center, barycenter, or designated position) of the tumor position of the future time phase from a reference position (such as a center, barycenter, or designated position) of the irradiation range. The deviation is supplied to the MRI integrated radiotherapy apparatus 6. The couch control circuitry 69 of the MRI integrated radiotherapy apparatus 6 controls the couch driver 86, and moves the top plate 84 to cancel the deviation. Accordingly, the tumor position can always be included in the irradiation range, and stoppage of irradiation can be avoided.

The processing circuitry 51 also moves the irradiation range so that the tumor position of the future time phase is included in the irradiation range. Specifically, the processing circuitry 51 calculates a deviation of the tumor position of the future time phase from the irradiation range of the present time phase. For example, the processing circuitry 51 calculates a deviation of a reference position (such as a center, barycenter, or designated position) of the tumor position of the future time phase from a reference position (such as a center, barycenter, or designated position) of the irradiation range. The deviation is supplied to the MRI integrated radiotherapy apparatus 6. The irradiation control circuitry 67 of the MRI integrated radiotherapy apparatus 6 controls the irradiator 81, and moves the irradiation range to cancel the deviation. The irradiation range may be moved by, for example, adjusting the positions of a plurality of blades constituting a multileaf collimator. Accordingly, the tumor position can always be included in the irradiation range, and stoppage of irradiation can be avoided.

In the above description, the trained model is described as outputting a tumor position of a future time phase in response to an input of an MR image of a present time phase. However, the present embodiment is not limited to this.

Figure 12:
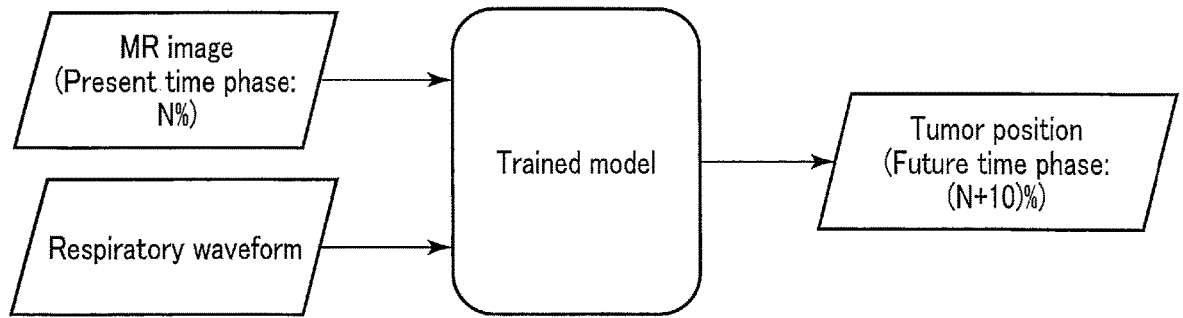
FIG. 12 is a diagram schematically showing an input and output of another trained model according to the present embodiment.

FIG. 12 is a diagram schematically showing an input and output of another trained model according to the present embodiment. The trained model shown in FIG. 12 is a neural network trained to output a tumor position of a future time phase (N+10)% in response to an input of a combination of an MR image of a present time phase N % and a respiratory waveform. The respiratory waveform to be input may include the range from the present time phase to a respiratory time phase at least one respiratory cycle before the present time phase. Through the input of the combination of the MR image and the respiratory waveform, an untrained model can learn a relationship between the input MR image and respiratory time phase; therefore, the estimation accuracy of the tumor position of the future time phase is expected to be improved.

The respiratory waveform is an example of information for ascertaining body movement of a patient. Instead of the respiratory waveform, a numerical value or symbol indicating the present time phase may be input, or a numerical value or symbol indicating a respiratory level corresponding to the present time phase may be input. Alternatively, instead of the respiratory waveform, a biological waveform, such as an electrocardiogram, which expresses an activity of a portion that rhythmically moves as a time waveform, may be input. Alternatively, instead of the respiratory waveform, outline data of a patient, which is generated by an optical scanner performing an optical scan on the patient, may be input.

Figure 13:
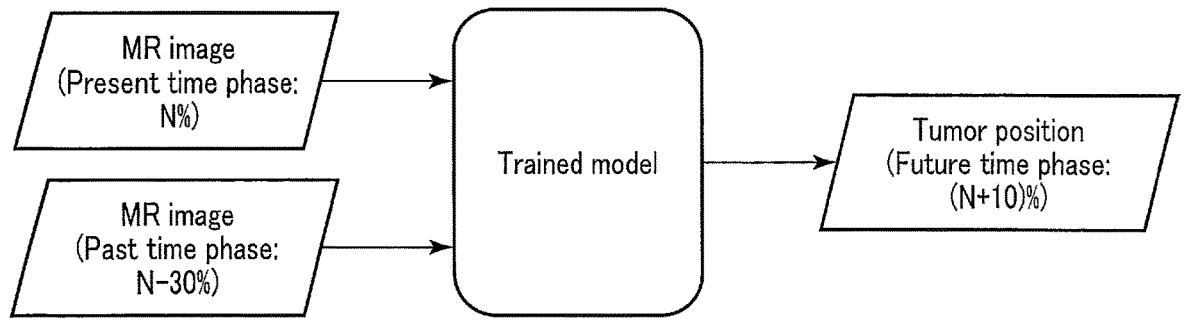
FIG. 13 is a diagram schematically showing an input and output of another trained model according to the present embodiment.

FIG. 13 is a diagram schematically showing an input and output of another trained model according to the present embodiment. The trained model shown in FIG. 13 is a neural network trained to output a tumor position of a future time phase (N+10)% in response to an input of a combination of an MR image of a present time phase N % and an MR image of a past time phase (N−30)%. The MR image of the past time phase (N−30)% is an MR image of a past time phase that is one frame before the present time phase N %, which is generated by the MRI integrated radiotherapy apparatus 6 with the frame rate of 30%. Through the input of the combination of the MR image of the present time phase and the MR image of the past time phase, an untrained model can learn a movement of the tumor region from the past time phase to the present time phase; therefore, the estimation accuracy of the tumor position of the future time phase is expected to be improved.

Figure 14:
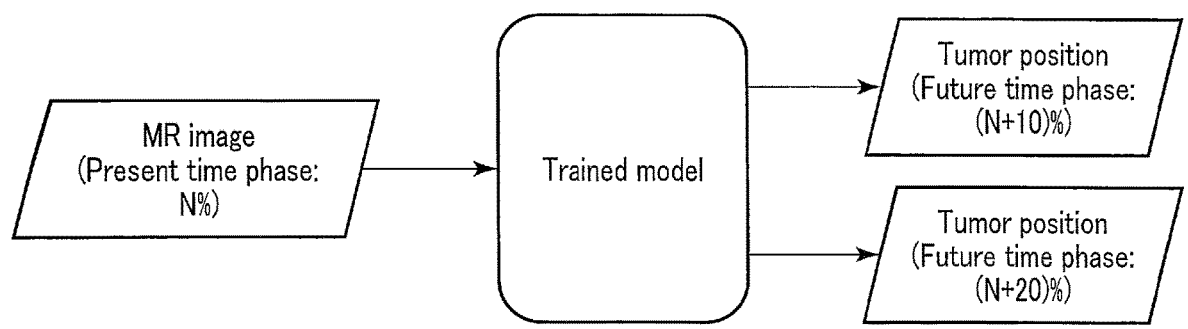
FIG. 14 is a diagram schematically showing an input and output of another trained model according to the present embodiment.

FIG. 14 is a diagram schematically showing an input and output of another trained model according to the present embodiment. The trained model shown in FIG. 14 is a neural network trained to output a tumor position of a future time phase (N+10)% and a tumor position of a future time phase (N+20)% in response to an input of an MR image of a present time phase N %. The MR image of the future time phase (N+20)% is an MR image of a time phase before, in time, a time phase one frame after the present time phase N %. Since a plurality of tumor positions of a plurality of future time phases are output, irradiation control can be temporally more densely performed in accordance with the tumor position.

As long as at least one time phase of the future time phases is a time phase before, in time, the time phase one frame after the present time phase No, the other future time phases may be time phases after, in time, the time phase one frame after the present time phase N %.

In the above embodiment, a tumor position of a future time phase is directly estimated by inputting an MR image of a present time phase to a trained model. However, the tumor position of the future time phase may be indirectly estimated from the MR image of the present time phase. For example, a trained model that outputs an MR image of a future time phase in response to an input of an MR image of a present time phase is used. In this case, the processing circuitry 51 inputs an MR image of the present time phase to the trained model and thereby estimates an MR image of a future time phase, extracts a tumor region included in the MR image of the future time phase by image processing or the like, and identifies the position of the extracted tumor region as the tumor position of the future time phase.

In the above embodiment, a tumor position of a future time phase is estimated by inputting an MR image of a present time phase to a trained model. However, the tumor position of the future time phase may be estimated from the MR image of the present time phase without using a trained model. For example, the processing circuitry 51 may apply rule-based data to the MR image of the present time phase to estimate the tumor position of the future time phase. Specifically, a tumor position is obtained in advance for each of a plurality of respiratory time phases of a patient to be treated, and a table in which a respiratory time phase is associated with a tumor position is created. The table is stored in the memory device 59. For estimation, the processing circuitry 51 identifies a tumor position from the MR image of the present time phase. The processing circuitry 51 also obtains a tumor position of the present time phase from the table, and calculates a differential value between the identified tumor position and the tumor position obtained from the table. Next, the processing circuitry 51 identifies a tumor position of a future time phase from the table, and estimates a tumor position of the future time phase by applying the calculated differential value to the identified tumor position of the future time phase.

As another example, a tumor position is obtained in advance for each of a plurality of respiratory time phases, and a difference (hereinafter referred to as a "relative tumor position") between the obtained tumor position and a given reference tumor position is calculated. The relative tumor position of each respiratory time phase is calculated regarding patients with various figures, and a statistic of the relative tumor positions of the patients with various figures is calculated for each respiratory time phase. Then, a rule-based database in which a respiratory time phase is associated with a statistic of relative tumor positions is created. The database is stored in the memory device 59 or the like. For estimation, the processing circuitry 51 identifies a tumor position from the MR image of the present time phase. On the other hand, the processing circuitry 51 obtains a statistic of relative tumor positions of a future time phase from the database, and corrects the statistic based on the figure of the patient to calculate a corrected relative tumor position. Then, the processing circuitry 51 applies the corrected relative tumor position to the tumor position of the present time phase, and thereby estimates a tumor position of the future time phase.

As another example, a tumor position of a future time phase may be estimated based on an MR image of a present time phase and respiratory waveform data of a patient to be treated. As another example, a tumor position of a future time phase may be estimated based on an MR image of a present time phase and outline data of a patient to be treated.

The processing circuitry 51 may also adjust the tumor position of the future time phase based on the difference between an estimated tumor position and an actual tumor position. The processing circuitry 61 of the MRI integrated radiotherapy apparatus 6 may also provide a respiratory guide for the patient based on the difference between an estimated tumor position and an actual tumor position.

The above-described trained models shown in FIGS. 4, 12, 13, and 14 may be combined as appropriate. For example, a model trained to output two tumor positions of two future time phases in response to an input of an MR image of a present time phase and an MR image of a past time phase may be used. Alternatively, a model trained to output one or two tumor positions of one or two future time phases in response to an input of an MR image of a present time phase, an MR image of a past time phase, and a respiratory waveform may be used. The number of MR images of past time phases to be input is not limited to one, and a model may be trained to receive an input of a plurality of MR images of a plurality of past time phases. The number of MR images of future time phases to be output is not limited to one or two, and a model may be trained to output three or more MR images of three or more past time phases.

The configuration of the radiotherapy system 100 shown in FIG. 1 is an example, and the present embodiment is not limited to this. For example, the irradiation control apparatus 5 may be incorporated into the MRI integrated radiotherapy apparatus 6. The machine learning apparatus 4 may be incorporated into the MRI integrated radiotherapy apparatus 6 or into the irradiation control apparatus 5. Regarding the MRI integrated radiotherapy apparatus 6, the magnetic resonance imaging apparatus and the radiotherapy apparatus need not necessarily be integrated with each other, and may be separated from each other.

As described above, the irradiation control apparatus 5 according to the present embodiment includes at least the processing circuitry 51. The processing circuitry 51 obtains an MR image of a first time phase, which includes a tumor region of a patient. The processing circuitry 51 inputs the MR image of the first time phase to a trained model, and estimates a position of the tumor region of the patient of a second time phase, which is a predetermined time phase after the first time phase. The trained model is a neural network trained based on an MR image including a tumor region and a position of the tumor region included in the MR image of a time phase that is a predetermined time phase after the time phase of the MR image. The processing circuitry 51 controls irradiation by the radiotherapy mechanism 8 based on the tumor position of the patient of the second time phase.

The above-described configuration enables irradiation control based on the position of the tumor region of the second time phase, which is a predetermined time phase after the first time phase, not based on the position of the tumor region included in the MR image of the first time phase. Even when the tumor region moves out of the irradiation range between frames of MR imaging for example, it is possible to detect in advance that the tumor region will move out of the irradiation range, and exposure that does not contribute to radiotherapy can be reduced. When the frame rate of MR images is low, the possibility that the tumor region will move out of the irradiation range between frames increases. Even in such a case, the present embodiment can reduce exposure that does not contribute to radiotherapy.

According to at least one of the above-described embodiments, the accuracy of irradiation control in radiotherapy can be improved.

The term "processor" used in the above description means, for example, a CPU, a GPU, or circuitry such as an application specific integrated circuit (ASIC), a programmable logic device (e.g., a simple programmable logic device (SPLD), a complex programmable logic device (CPLD), or a field programmable gate array (FPGA)). The processor reads and executes a program stored in memory circuitry to implement a function. Instead of storing a program in memory circuitry, a program may be directly integrated in circuitry of the processor. In this case, the processor implements the function by reading and executing the program integrated in the circuitry. The function corresponding to the program may be implemented by a combination of logic circuits instead of executing the program. The processors described in connection with the above embodiments are not limited to single-circuit processors; a plurality of independent processors may be integrated into a single processor that implements the functions of the processors. Furthermore, multiple structural components in FIGS. 1, 2, and 3 may be integrated into a single processor in order to implement the functions of the structural components.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An irradiation control apparatus comprising:
   processing circuitry configured to:
   obtain time-series MR images acquired at predetermined intervals and including a tumor region of a patient;
   input an MR image of a first time phase among the time-series MR images to a trained model to estimate a position of the tumor region of the patient of a second time phase,
   the second time phase being after the first time phase and before a time phase at which a period corresponding to each of the predetermined intervals has elapsed since the first time phase, the trained model being a neural network trained to output, upon receiving an input of a tumor region-containing MR image, a later-time-phase position of a tumor region included in the input tumor region-containing MR image, the later-time-phase position being of a time phase after a time phase of the input tumor region-containing MR image; and control irradiation by a radiotherapy apparatus based on the estimated tumor position of the second time phase.

2. The irradiation control apparatus according to claim 1, wherein the MR image of the first time phase is an MR image of one time phase of time-series MR images generated by a radiotherapy apparatus in which a magnetic resonance imaging apparatus is incorporated performing MR imaging on the patient.

3. The irradiation control apparatus according to claim 2, wherein the predetermined intervals correspond to a frame rate at which the magnetic resonance imaging apparatus performs dynamic imaging.

4. The irradiation control apparatus according to claim 1, wherein the processing circuitry obtains a biological waveform or outline data of the patient, and estimates the position of the tumor region of the second time phase based on the MR image of the first time phase and the biological waveform or outline data.

5. The irradiation control apparatus according to claim 1, wherein the processing circuitry estimates the position of the tumor region of the second time phase by inputting the MR image of the first time phase and an MR image of a time phase one or more frames before the first time phase to the trained model.

6. The irradiation control apparatus according to claim 1, wherein the processing circuitry causes a display device to display the estimated position of the second time phase, the estimated position of the second time phase and an irradiation range being displayed on the MR image of the first time phase.

7. The irradiation control apparatus according to claim 1, wherein the processing circuitry determines whether or not the estimated position of the second time phase is outside an irradiation range, and supplies an irradiation stop command to the radiotherapy apparatus when the processing circuitry determines that the estimated position of the second time phase is outside the irradiation range.

8. The irradiation control apparatus according to claim 1, wherein the second time phase includes a plurality of second time phases which are after the first time phase by respective periods within the period corresponding to each of the predetermined intervals, and the processing circuitry estimates positions of a plurality of tumor regions relating to the second time phases.

9. The irradiation control apparatus according to claim 1, wherein the processing circuitry estimates the position of the tumor region of the second time phase using rule-based data.

10. The irradiation control apparatus according to claim 1, wherein the processing circuitry estimates the position of the tumor region of the second time phase based on biological waveform data of the patient.

11. The irradiation control apparatus according to claim 1, wherein the processing circuitry estimates the position of the tumor region of the second time phase based on outline data of the patient.

12. The irradiation control apparatus according to claim 1, wherein the processing circuitry adjusts a position to be estimated next, based on a difference between the estimated position and an actual position of the tumor region.

13. A radiotherapy system comprising:

an irradiation apparatus configured to irradiate a patient;

an imaging apparatus configured to perform MR imaging on the patient and generate first time-series MR images including a tumor region of the patient;

processing circuitry configured to input an MR image of a first time phase among the first time-series MR images to a trained model to estimate a position of the tumor region of the patient of a second time phase, the second time phase being after the first time phase and before a time phase at which a period corresponding to each of the predetermined intervals has elapsed since the first time phase, the trained model being a neural network trained to output, upon receiving an input of a tumor region-containing MR image, a later-time-phase position of a tumor region included in the input tumor region-containing MR image, the later-time-phase position being of a time phase after a time phase of the input tumor region-containing MR image; and control circuitry configured to control the irradiation apparatus based on the estimated position of the second time phase.

14. The radiotherapy system according to claim 13, further comprising a machine learning apparatus, wherein the imaging apparatus performs dynamic imaging on a subject at a predetermined frame rate and generates second time-series MR images, and the machine learning apparatus generates the trained model based on a training sample including an MR image of the first time phase among the second time-series MR images and a position of a tumor region included in an MR image of the second time phase among the second time-series MR images.

15. The radiotherapy system according to claim 14, wherein the imaging apparatus performs dynamic imaging at the predetermined frame rate a plurality of times while varying imaging timing to generate the second time-series MR images.

16. The radiotherapy system according to claim 15, wherein the control circuitry guides respiration of the patient based on a difference between the estimated position and an actual position of the tumor region.

17. An irradiation control method comprising:

inputting, by a computer, an MR image of a first time phase to a trained model to estimate a position of a tumor region of a patient of a second time phase, the MR image of the first time phase including the tumor region of the patient, the second time phase being after the first time phase and before a time phase at which a predetermined period has elapsed since the first time phase, the trained model being a neural network trained to output, upon receiving an input of a tumor region-containing MR image, a later-time-phase position of a tumor region included in the input tumor region-containing MR image, the later-time-phase position being of a time phase after a time phase of the input tumor region-containing MR image; and controlling, by the computer, irradiation by a radiotherapy apparatus based on the estimated tumor position of the second time phase.

\* \* \* \* \*